United States Patent
Mullins et al.

[11] Patent Number: 5,201,220
[45] Date of Patent: Apr. 13, 1993

[54] APPARATUS AND METHOD FOR DETECTING THE PRESENCE OF GAS IN A BOREHOLE FLOW STREAM

[75] Inventors: Oliver C. Mullins, Ridgefield, Conn.; Daniel R. Hines, Lawrenceville, N.J.; Masaru Niwa, Kawasaki, Japan; Kambiz A. Safinya, Garches, France

[73] Assignee: Schlumberger Technology Corp., New York, N.Y.

[21] Appl. No.: 942,005

[22] Filed: Sep. 8, 1992

Related U.S. Application Data

[62] Division of Ser. No. 574,317, Aug. 28, 1990, Pat. No. 5,167,149.

[51] Int. Cl.⁵ .................. E21B 49/08; G01V 9/00
[52] U.S. Cl. ..................... 73/155; 250/269; 73/19.01
[58] Field of Search ........... 73/64.55, 61.41, 61.48, 73/155, 24.02, 19.01; 250/269

[56] References Cited

U.S. PATENT DOCUMENTS

| | | | |
|---|---|---|---|
| 2,727,997 | 12/1955 | Schofield | 73/61.48 |
| 3,422,667 | 1/1969 | Hrdina | 73/53.01 |
| 3,530,711 | 9/1970 | Tocanne | 73/155 |
| 3,859,851 | 1/1975 | Urbanosky | 73/155 |
| 3,899,688 | 8/1975 | Périères | 73/61.48 |
| 4,436,420 | 3/1984 | Depp et al. | 356/361 |
| 4,622,845 | 11/1986 | Ryan et al. | 73/24.02 |
| 4,860,581 | 8/1989 | Zimmerman et al. | 73/155 |
| 4,918,979 | 4/1990 | Pearce et al. | 73/61.41 |
| 4,936,139 | 6/1990 | Zimmerman et al. | 73/155 |
| 4,974,552 | 12/1990 | Sickafus | 73/61.43 |
| 4,994,671 | 2/1991 | Safinya et al. | 250/255 |

FOREIGN PATENT DOCUMENTS

| | | |
|---|---|---|
| 0289833 | 4/1988 | European Pat. Off. |
| 2578978 | 9/1986 | France. |
| 60-11636 | 1/1986 | Japan. |
| 63-132139 | 6/1988 | Japan. |
| 1514977 | 6/1978 | United Kingdom ........... 73/61.48 |
| 2199404 | 11/1986 | United Kingdom. |

Primary Examiner—Hezron E. Williams
Assistant Examiner—George Dombroske
Attorney, Agent, or Firm—Leonard W. Pojunas

[57] ABSTRACT

A borehole apparatus detects the presence of gas within a formation fluid sample. A light source transmits light rays to an interface between the fluid sample and the flow line. The interface reflects the light rays toward a detector array. The detector array detects light rays having angles of incidences extending from less than the Brewster angle to more than the critical angle for gas. A data base stores information concerning the Brewster angle and critical angle of gas for a plurality of gas volume categories. A processor determines the percentage of gas present in the formation fluid sample and categorizes the fluid sample as high as, medium gas, low gas, and no gas based on the signal from the detector array and the information from the data base.

10 Claims, 5 Drawing Sheets

APPARATUS AND METHOD FOR DETECTING THE PRESENCE OF GAS IN A BOREHOLE FLOW STREAM

This is a divisional application of copending U.S. Ser. No. 07/574, filed Aug. 28, 1990 for "Apparatus and Method for detecting the Presence of Gas in a Borehole Flow Stream".

The invention concerns an apparatus and a method for analyzing the composition of multiphase formation fluids and more specifically concerns an optical apparatus and method for detecting the presence of gas in a flow stream that comprises oil, water, gas or particulates within a borehole.

FIELD OF THE INVENTION

U.S. Pat. No. 4,860,581 to Zimmerman et al. ("the Zimmerman patent") concerns a downhole tool for the detection of formation properties. The Zimmerman patent is assigned to the same assignee as this invention. The tool of the Zimmerman patent measures pressure in the borehole during drawdown and buildup tests to estimate permeability based on an assumption that flowing fluid is incompressible. However, this is not the case. The pressure drop is actually quite large, a few thousand psi being typical. Many formation crude oils, particularly those under a gas cap, will evolve gas under such a pressure drop. In fact, individual pressure buildup curves are inconsistent when incompressible fluid flow is assumed.

Differential flow velocities between gas and liquid phases can be large due to their very different viscosity and density. Thus, when gas evolves in formation fluids, samples of formation fluid may not accurately represent the composition of the formation fluid. When gas evolves, the resulting sample can be enriched in light hydrocarbons compared to formation crude oil. Gas bubbles can block pores, reducing permeability and gas that evolves in the formation can reduce gas drive.

Japanese patent No. 61-11636, entitled Liquid Discriminating Sensor, describes a refractometer which determines the index of refraction of a substance by determining the critical angle. Significant differences exist between the Gas Detector of this invention and the Liquid Discriminating Sensor in both purpose and design. The purpose of the Liquid Discriminating Sensor is to determine the identity of the only component of a liquid sample. The Liquid Discriminating Sensor does not work for multiphase samples. The Liquid Discriminating Sensor measures the unknown index of refraction of a liquid sample with high precision in order to distinguish between the similar indices of refraction of different liquids, thereby determining sample identity. The cost of the high precision is that only a limited angular range can be covered.

Thus, the detection of gas phase and the categorizing of percent gas volumes of the formation fluid would improve permeability estimates, sampling accuracy, and production pressure estimates. The downhole detection of gas in the flow stream would allow a more accurate determination of bubble point using pressure gauges and the determination of the minimum pressure at which the formation can be produced.

OBJECTS AND SUMMARY OF THE INVENTION

It is therefore an object of the invention to provide an apparatus for determining the presence of gas within formation fluid that may include water, gas, oils and particles.

It is another object of the invention to provide a downhole apparatus for determining in situ the presence of gas within the formation fluid.

It is another object of the invention to provide an apparatus that uses light for detecting the presence of gas in a formation fluid.

In one embodiment, the invention comprises a borehole apparatus and a method for categorizing volumes of gas in a multiphase fluid obtained from a formation. The fluid comprises at least one of oil, water, and gas. The apparatus preferably comprises a flow line for containing the fluid and a light source for transmitting light toward the fluid in the flow line. A prism transmits light from the source to the fluid and forms an interface with the flow line. The interface reflects light from the source and a detector array detects the light. A data base stores information relating to a plurality of categories of determined gas volumes of formation fluid. A processor obtains data concerning the reflected light from the detector array and the information from the data base to determine a category of gas volume of the fluid in the flow line. The purpose of the Gas Detector is to detect the presence of gas in a multiphase flow stream. The flow may contain gas, immiscible liquids, such as oil and water, and solids, such as sand and clay. In addition, the flow stream can be quite erosive. The Gas Detector must also work under conditions of very high pressure, up to 20,000 psi. Due to the high pressures, the gas density can become appreciable; correspondingly the gas index can become large ($\sim 1.2$). Knowledge of the pressure and temperature provides the index of refraction of the (natural) gas. The Gas Detector detects the presence of gas of known index of refraction. Thus the Gas Detector does not measure the index of refraction of the multiphase flow stream to determine the flow stream constituents. As such, the gas detector is not a refractometer.

In addition to the different purposes of the Gas Detector and the Liquid Discriminating Sensor, there are significant design differences. The Gas Detector must cover a wide angular range; thus a light source of very large numerical aperture is needed ($\sim 0.6$). Constraints on the optical design are also imposed by the high pressures attainable in the flow stream, which must be supported by the optical window. In the optical design of the Liquid Discriminating Sensor, the window depicted would not be able to withstand a high pressure, erosive flow stream like that in a borehole.

In addition, the large angular range necessitated for high and variable pressure gas detection would be very difficult to achieve with the optical design of the Liquid Discriminating Sensor. The Gas Detector employs a source of numerical aperture (NA) of $\sim 0.6$; a lens providing this NA would have an F number of 0.8 for collimated light source. To achieve the same NA and image distance with the point source of the Liquid Discriminating Sensor, the lens must be even faster. Lenses that are this fast are very difficult to work with and are frequently ineffective in achieving large NA due to reflection losses for the marginal light rays. In addition, the retaining force that must be applied to the sapphire window places significant limitations on the design and location of the lens. Finally, when sampling multiphase flow streams, inaccurate results are easily obtained if a single point of the flow stream is sampled in the manner of the Liquid Discriminating Sensor. The Gas Detector samples an entire area of the flow stream-sapphire interface, thus making the Gas Detector much less susceptible to inaccuracies resulting from droplets or films on a window at that interface. The Gas Detector is a unique device which satisfies a recently developed niche in the oil field.

DETAILED DESCRIPTION

The invention is applicable to both production logging and borehole investigative logging.

Figure 1:
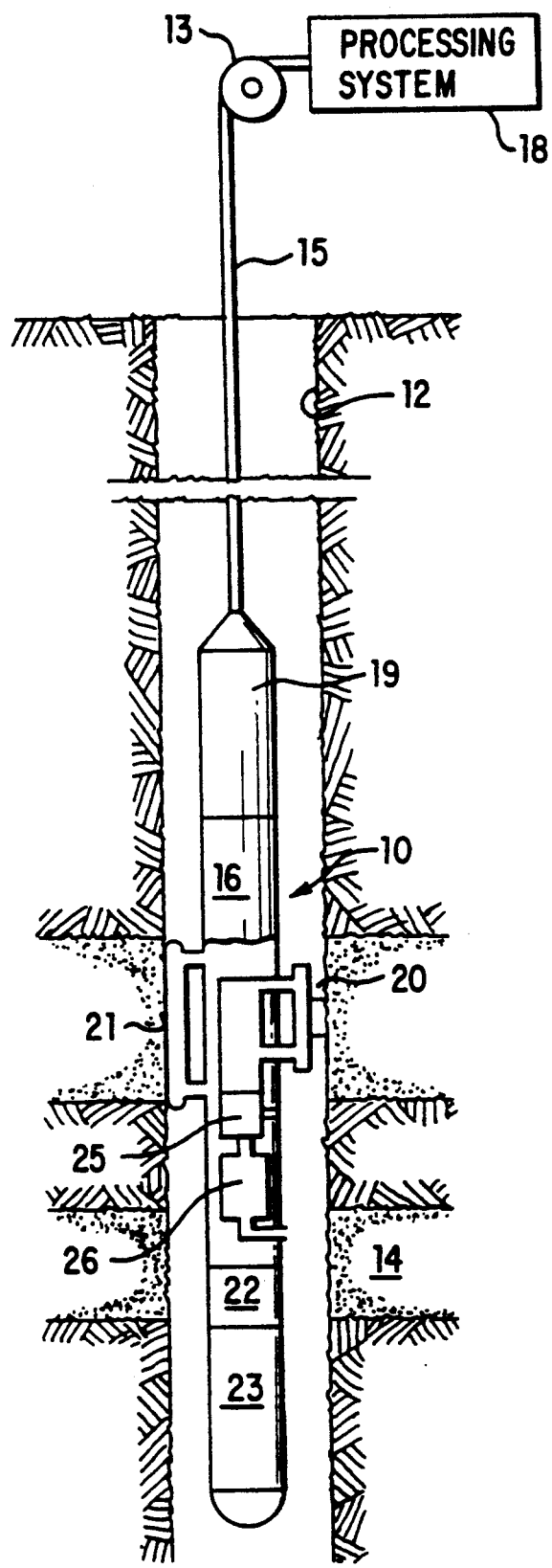
FIG. 1 is a schematic diagram of a borehole logging tool having a gas detector module for analyzing the composition of a formation fluid.

FIG. 1 is a schematic diagram of a borehole logging tool 10 having a gas detector module for analyzing the composition of a fluid from a formation 14. The borehole logging tool 10 hangs from the lower end of a multiconductor cable 15 in a borehole 12. A winch 13 on the Earth's surface spools the multiconductor cable 15 in the usual manner. On the surface, the multiconductor cable 15 electronically connects to a processing system 18. The processing system 18 receives data over the multiconductor cable 15 and analyzes the data to determine gas concentrations, as described below.

The logging tool 10 has a elongated body 19. The body 19 contains an assembly 20 that extends from the body 19 for admitting fluid into the body 19. The body 19 also contains another assembly 21 that extends from the body 19 for anchoring the body 19 in the borehole 12. These two assemblies 20 and 21 preferably extend from opposite sides of the body 19. The assembly 20 for admitting fluid seals off or isolates selected portions of the wall of the borehole 12 to establish pressure or fluid communication with an adjacent earth formation. U.S. Pat. Nos. 4,396,254 and 3,859,851 describe suitable assemblies for obtaining fluids and are assigned to the assignee of this invention. The disclosures of those patents are incorporated by reference.

Fluid admitted by the assembly 20 flows through a module 25 of the logging tool 10 that analyzes the composition of the formation fluid. U.S. patent application Ser. No. 07/418,748 describes a suitable embodiment of such a module and is assigned to the same assignee as this invention. The disclosure of that application is incorporated by reference. The fluid also flows through a gas detector module of the logging tool 10. The fluid then exits the logging tool 10 through a port (not shown) or travels to one or more collecting chambers that receive and retain fluids obtained from the formation 14. The processing system 18 and a downhole system 16 control the assembly for admitting fluids, the assembly for anchoring the body, the analyzer module, gas detector module, and the flow path to the collecting chambers.

Figure 2:
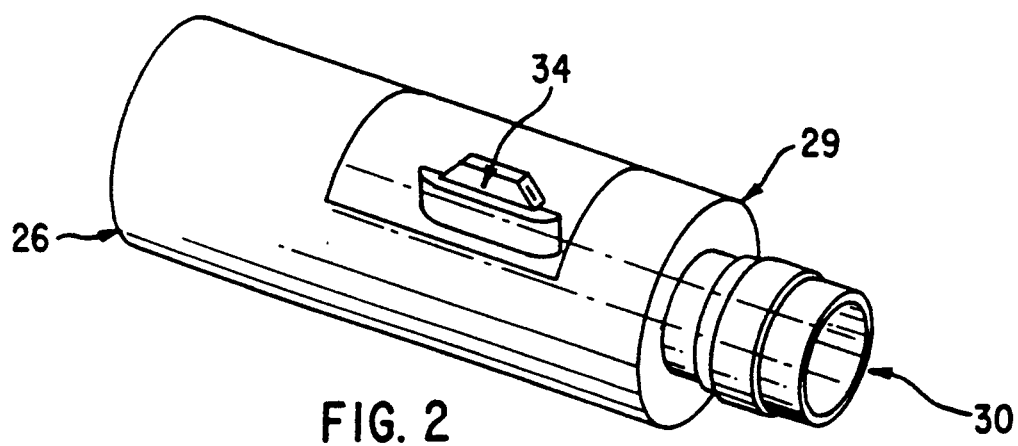
FIG. 2 is a perspective cutaway view of the gas detector module of FIG. 1.

FIG. 2 is a cut-away perspective view of a gas detector module 26 according to this invention. The gas detector module 26 comprises a high pressure cell 29 of stainless steel that encloses the high pressure flow line and other internal components of the gas detector module 26 within the borehole environment, for example. One internal component of the gas detector module 26 is a flow line, such as 30 of FIG. 3, that contains the formation fluid in the module for analysis of the fluid. The flow line 30 is considered to contain any fluid that is held by or flows through the flow line 30. The flow line 30 has a window that comprises an optical element such as a prism 34. A surface of the prism 34 contacts the formation fluid in the flow line 30, creating an optical interface 34a between the prism 34 and the fluid. The interface 34a refracts light into the fluid and reflects light in an optical system as described below concerning FIG. 3. Preferably, the prism 34 is sapphire, which is transparent to near-infrared and visible light and is resistant to abrasion by the formation fluid.

Figure 3:
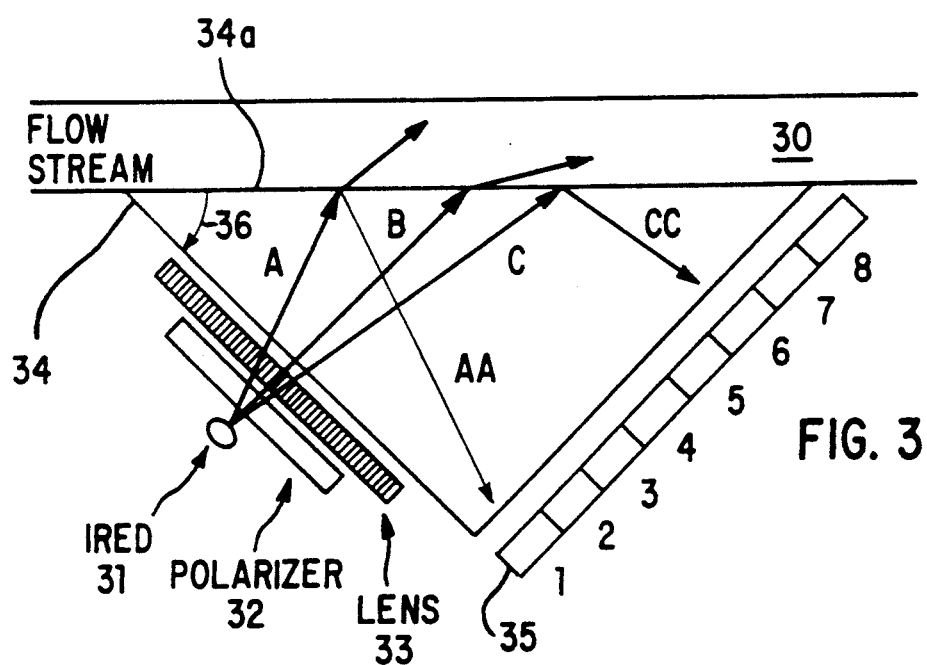
FIG. 3 is a schematic diagram of the gas detector module of FIGS. 1 and 2.

FIG. 3 is a schematic diagram of an optical system comprising the gas detector module 26 of FIG. 2 according to this invention. The inventors have found that by arranging a prism and detectors to monitor reflected intensity of light in an angular range that extends from less than the Brewster angle to more than the critical angle for gas, the presence of gas in the formation fluid is revealed, as described below.

The optical system includes a light source 31 that generates light toward formation fluid contained in the flow line 30. The light source 31 comprises an infrared emitting diode or a light emitting diode, for example. The light generated by the light source 31 has sufficient angular width for compatibility with other components of the optical system, which are described below.

The light source 31 transmits light to a p-polarizing filter 32. P-polarized light is preferred over s-polarized or unpolarized light because p-polarized light enhances contrast of light that passes through a cylindrical lens 33 and reflects from the interface 34a in an angular range between a Brewster angle and a critical angle. A Brewster angle is the angle of incidence of light that reflects from a surface at which the reflectivity for light having an electrical vector in the plane of incidence becomes zero. The critical angle is the smallest angle of incidence at which total internal reflection from an interface occurs.

The cylindrical lens 33 forces the light only on the interface 34a between the prism 34 and the formation fluid, and not on the sides of the cell 29 nor any part of the prism 34 that contacts the body 19 of the cell 29. Focusing the light increases the intensity of the light that is transmitted to and reflected from the interface 34a between the formation fluid and the prism 34. Light, such as rays A, B, and C, then enters the prism 34 and strikes the interface 34a at a desired range of angles of incidence that extends from less than the Brewster angle to greater than the critical angle of gas in the flow stream in the vicinity of the interface 34a. The related light rays are then transmitted through the opposite face of the prism 34 to an array of detectors 35.

The array of detectors comprises a linear array of eight photodetectors 1–8 that are sensitive to infrared light, in one embodiment. Each detector 1–8 of the array 35 is positioned to receive light that is reflected by the interface 34a at a corresponding angle of reflectance. Accordingly, the array 35 of detectors is positioned such that each detector 1–8 is illuminated by light rays of a particular angle of reflection and, thus, of a particular angle of incidence. In another embodiment, one detector can be used instead of an array of detectors to detect light between the Brewster angle and the critical angle. Also, a polarizing filter can be placed at the single detector or array of detectors, instead of between the light source 31 and the cylindrical lens 33.

For example, light rays, such as A, that intersect the interface 34a nearest the light source 31 have relatively small angles of incidence. Accordingly, a substantial amount of light ray A enters the flow stream and the interface 34a reflects a small amount AA of the ray toward the detector 1. Light rays, such as C, that intersect the interface 34a farther from the light source 31 have larger angles of incidence and are entirely reflected by the interface 34a. None of light ray C enters the flow stream in the flow line 30 because the interface 34a reflects all of the ray toward another detector 8, assuming the flow line is filled with a gas. The interface 34a reflects all of the light ray C because this ray is at the critical angle of gas, for instance.

Figure 4:
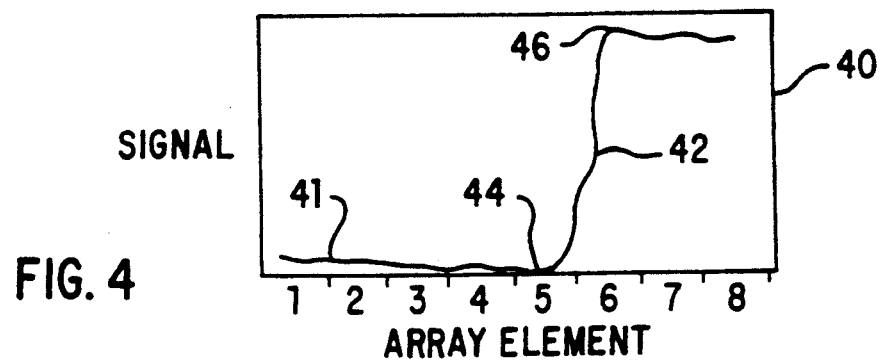
FIG. 4 illustrates output signals of an array of photodetectors in the gas detector module of FIGS. 2 and 3.

FIG. 4 plots a curve 42 that represents the output signal for each detector 1–8 in an array of detectors. The output signal for each detector 1–8 indicates the intensity of the light received by each corresponding detector of FIG. 3. For example, the low intensity light ray AA that the interface 34a reflects towards detector 1 appears as a low amplitude signal 41 in the plot of FIG. 4 for detector 1. The full intensity light ray CC that the interface 34a reflects towards detector 6 appears as the peak signal 46 in the plot of FIG. 4 for detector 6. This peak signal 46 represents the critical angle of gas of the flow stream in the flow line 30. The curve 42 of FIG. 4 also indicates the Brewster effect at 44 where the signal falls to zero. This zero signal is the output of detector 5.

Figure 5:
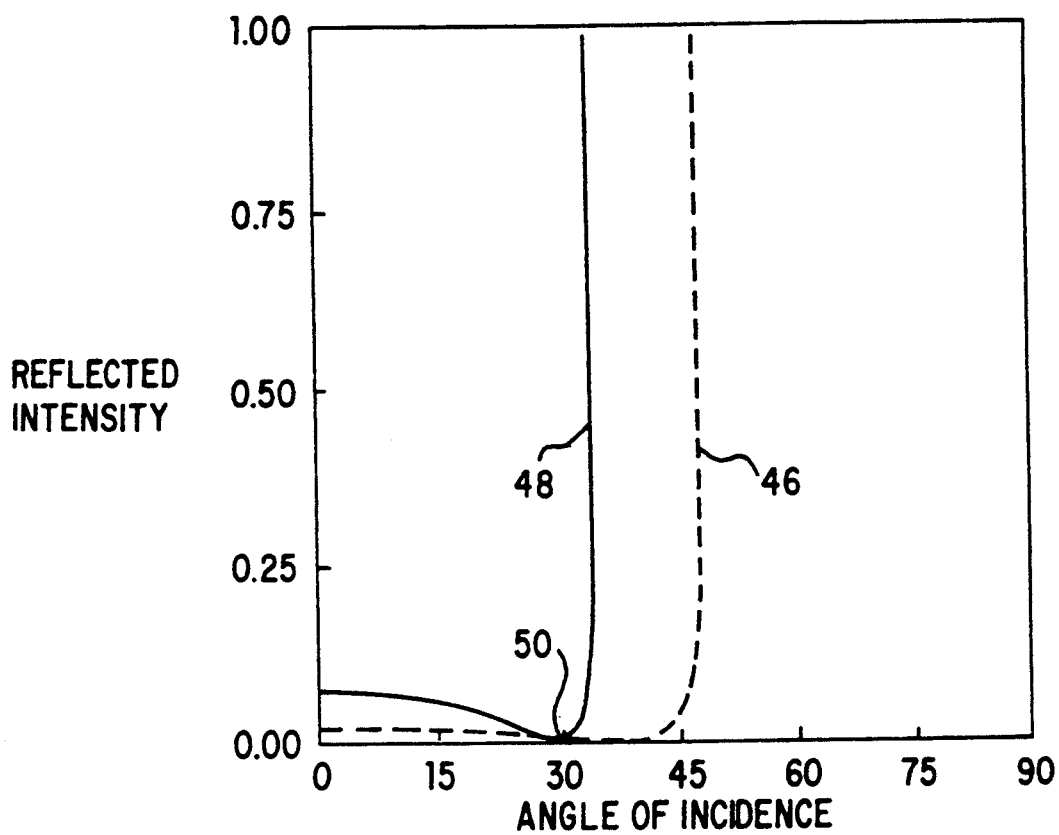
FIG. 5 illustrates a plot of reflected intensity verses angle of incidence of light incident on an interface between a sapphire prism and water, and gas.

FIG. 5 illustrates the relationship between reflected light intensity and the angle of incidence for light that is incident on an interface, such as 34a, between a sapphire lens and water, shown as a dashed curve 46, and gas, shown as a solid curve 48. In the gas curve 48, a sharp transition 50 occurs from a zero signal at approximately 30 degrees incidence, the Brewster angle, toward the critical angle. This transition 50 in the curve 48 of FIG. 5 corresponds to the zero signal 44 in the curve 42 of FIG. 4. At 30 degrees incidence the water curve 46 has a broad minimum and little variation in intensity. An oil curve would have a similar broad minimum.

When only water or oil is present in the formation fluid, the detectors of the array 35 would indicate the presence of little if any light, because water and oil would reflect light at a great angle of incidence. Such an angle of incidence would be outside the range extending from the Brewster angle to the critical angle for gas, and to which the detectors 1–8 are responsive. For example, the water curve 46 of FIG. 5 indicates that water in a flow line would reflect light at greater than 45 degrees incidence, which is outside such a range.

As described below concerning FIGS. 6–8, the processing system 18 receives and examines the output of the detector array 35 and correlates a peak intensity of reflected light to the critical angle for gas and a zero intensity to the Brewster angle of gas. The processing system 18 then examines the slope and other characteristics of the resulting curve between these angles to categorize gas volumes of the multiphase fluid formation in the flow line 30.

Preferably, a computer program executes steps to examine the output of the detector array 35 and the resulting curves. However, a microprocessor or a microcomputer could also perform these steps. The processing system 18 preferably includes a data base that stores information that corresponds to the data represented by the FIGS. 4, 5, 7, and 8, for example. The processing system compares the output of the detector array 35 to the information of the data base to label the fluid in the flow line as one of four gas volume categories. The data base could comprise a look-up table in an EPROM or data values in a computer program, for example. The data base can be located on the surface with the processor or as a separate element downhole with the logging tool 10.

The effects of flow stream geometry must be considered for optimum use of this invention. For equal gas volume fractions of fluid flow, the gas detector responds differently to slug flow streams compared to bubble or foam flow streams. For slug flow streams, the detector sees 100% gas passing through the flow line 30, then 100% water, for example. However, the average of a signal from the gas detector is linear in relation to gas volume fraction.

For bubble or foam flow streams, the gas detector sees some amount of liquid and gas bubbles at a variety of depths of the flow stream. Bubbles passing the prism 34 reflect light toward the detectors 1–8 differently than when no bubbles are present at the flat interface 34a between the prism 34 and gas in the flow line 30. These different reflections and bubble depths cause the output signal from the detectors 1–8 to deviate from the signal that would occur for a slug flow stream having the same gas volume fraction. In addition, the contents of the gas detector cell 29 also affect the output signal of the gas detector module 26. For example, due to the different slip velocities of gas, liquids and solids over the prism surface of the cell 29, the composition of cuts of the formation fluid can differ from the actual contents of the cell 29. For this reason, results produced by the gas detector module 26 must be viewed as semiquantitative instead of quantitative, and a process for analyzing resulting data is required.

Figure 6:
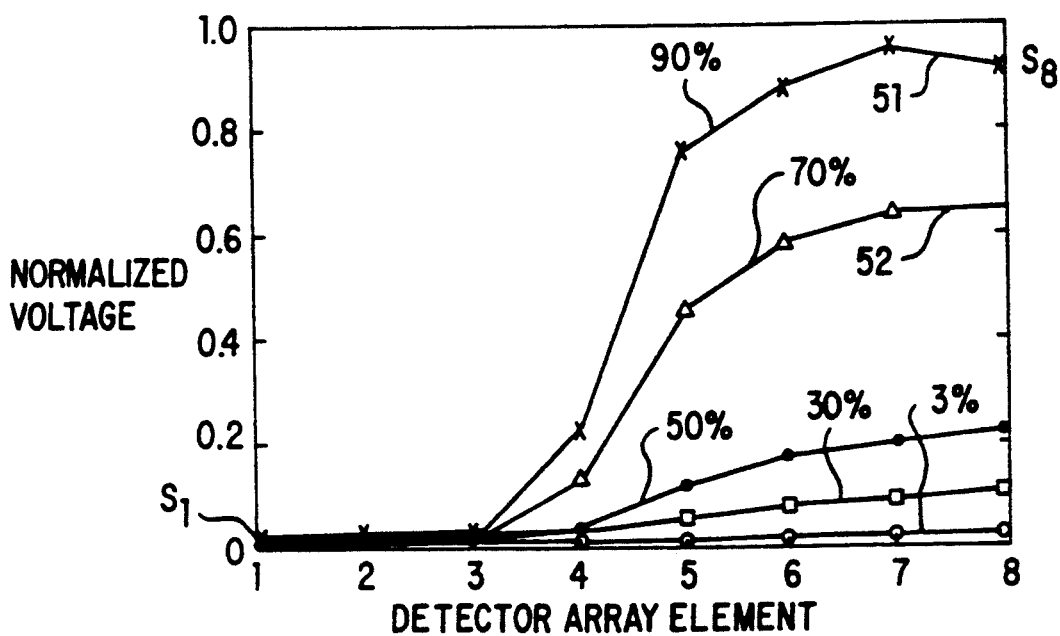
FIG. 6 illustrates a plot of gas detector signal verses gas volume fraction for flow streams containing crude oil and gas.

FIG. 6 illustrates gas volume fractions of 90% and 70% of multiphase fluids with curves 50 and 52, respectively. Curves 50 and 52 indicate large gas step heights of approximately 0.91 and 0.62, respectively. FIG. 6 also illustrates gas volume fractions of 50%, 30% and 3% with curves 54, 56, and 58, respectively. Curves 54, 56, and 58 indicate gas step heights of approximately 0.20, 0.08, and 0.01, respectively. The gas step heights of these curves are used to distinguish between gas volume categories of a multiphase fluid flow, as discussed below.

Figure 7:
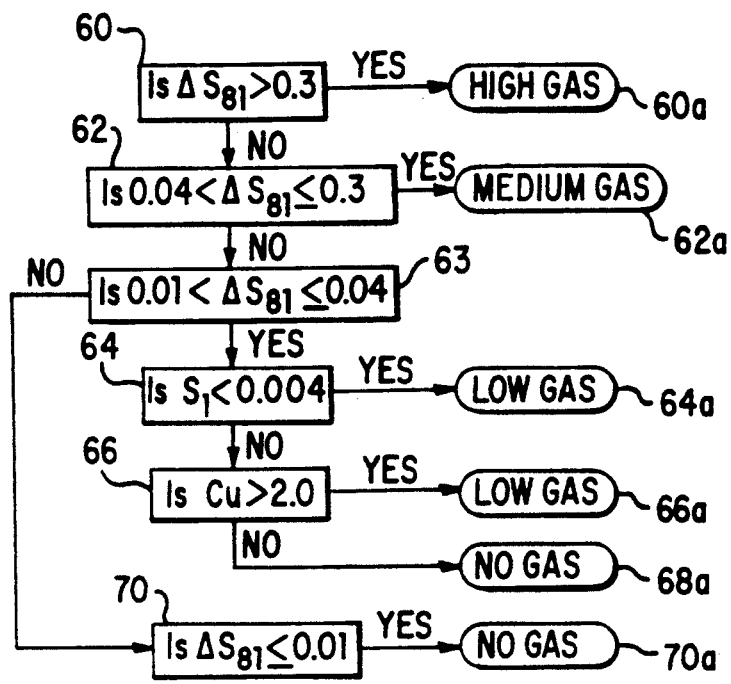
FIG. 7 illustrates a flow chart of steps that the gas detector of FIGS. 1-3 follows in categorizing the volume of gas in the flow stream.

FIG. 7 is a flow chart illustrating steps for analyzing output signals from the detector array 35. A variety of flow stream geometries and gas volume fractions were studied by the inventors to develop the steps of this process. Application of the steps to output signals of the detector array and to information in the data base of the processing system 18 is used to categorize formation fluid into four categories of gas volume fraction: high gas, medium gas, low gas, and no gas.

To determine high gas and medium gas volume categories, it is necessary to consider only gas step height $\Delta S_{81}$. Gas step height $\Delta S_{81}=S8-S1$, where S8 is the normalized voltage of the output signal produced by a detector corresponding to a large angle of incidence (in this case detector 8), and S1 is the normalized voltage of the output signal produced by a detector corresponding to a small angle of incidence (in this case detector 1). The gas step height increases monotonically with gas volume fraction and is, therefore, most noticeable at the high gas and medium gas volume categories.

If gas step height $\Delta S_{81}$ is larger than 0.3 (where 1 is full scale), as in block 60 of FIG. 7, the associated flow stream is labeled as high gas content, as indicated by block 60a. This label mostly represents flow streams with gas volume fractions larger than 70%. If $\Delta S_{81}$ is less than or equal to 0.3 and greater than 0.04, as shown in block 62, the associated flow stream is labeled as a medium gas content, as indicated by block 62a. This label mostly represents flow streams with gas volume fractions between 11% and 60%. If the gas step height is less than or equal to 0.04, as shown in block 63, further analysis is required to distinguish between low gas and no gas volume categories.

To fully distinguish between low gas and no gas categories, it is necessary to consider both baseline shift $S_1$ and curvature Cu, along with the gas step height $\Delta S_{81}$. Baseline shift S1 is the normalized voltage of the output signal received from detector 1. Curvature Cu is roughly the ratio of the slope of the curve between the Brewster angle and the critical angle, in this case the difference between the output signals of detectors 5 and 3 as indicated by FIG. 6, and the slope of the curve prior to the Brewster angle, in this case the difference between the output signals of detectors 3 and 1, for example.

The inventors have studied a large number of flow streams to develop an empirical means of distinguishing between flow streams containing low gas volume fractions and multiphase flow streams containing very little or no gas, such as emulsions. The different curvatures and baselines of curves representing such flow streams are used to distinguish between low gas and no gas categories. Emulsion streams containing no gas exhibit a curvature Cu similar to flow streams of low gas fraction, but have a larger baseline shift. Flow streams of emulsions containing small amounts of gas have a baseline shift similar to emulsions containing no gas but exhibit larger curvatures Cu.

Figure 8:
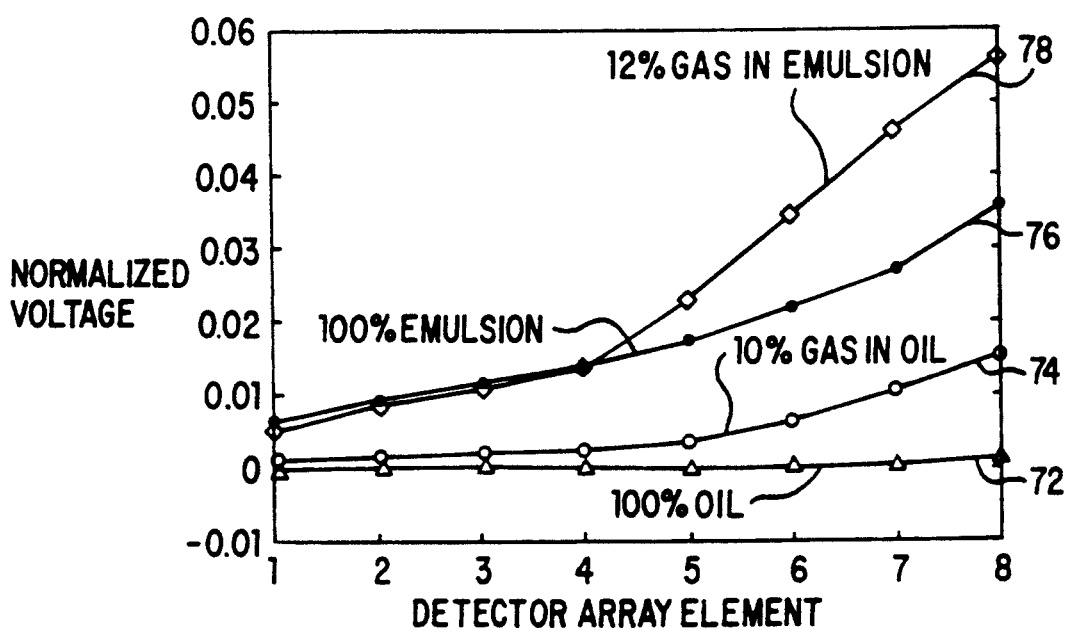
FIG. 8 illustrates a plot of gas detector signal verses low gas volume fraction and emulsion flow streams.

FIG. 8 illustrates normalized voltages of detector output signals for low gas fraction and emulsions flow streams. Curve 72 and curve 76 respectively represent flow streams of 100% oil and flow streams of 100% emulsion. Curve 76 indicates that a flow stream of 100% emulsion has a baseline shift S1 of approximately 0.036. Curve 72 indicates that a flow stream of 100% oil has a baseline shift of approximately 0.001.

Thus, if $\Delta S_{81}$ is less than or equal to 0.04 and greater than 0.01, as in block 63 of FIG. 7, and the baseline shift S1 is small S1<0.004, as in block 64 of FIG. 7, the associated flow stream is labeled as low gas content, as indicated by block 64a. If the baseline shift S1 is not small $S_1>0.004$ and the curvature is large Cu>2, as in block 66 of FIG. 7 the associated flow stream is also labelled as having low gas content, as indicated by block 66a. This label mostly represents flow streams with gas volume fractions between 1% and 10%. However, if the baseline shift is not small S1>0.004 and the curvature is small Cu<2, the associated flow stream is labeled as having no gas content, as indicated by block 68a. Finally if $\Delta S_{81}$ is less than or equal to 0.01, as in block 70 of FIG. 5, the associated flow stream is labeled as having no gas content, as indicated by block 70a. This label represents flow streams having a gas volume fraction of 0%.

Because the steps illustrated by FIG. 7 have been developed empirically from data using a specific gas detector geometry, the exact values of gas step height $\Delta S_{81}$, baseline shift $S_1$, and curvature Cu which determine the gas amount categories may change. Nevertheless, the basic concept of using the gas step height, baseline shift, curvature to determine gas volume categories is still applicable for different hardware configurations.

Figure 9:
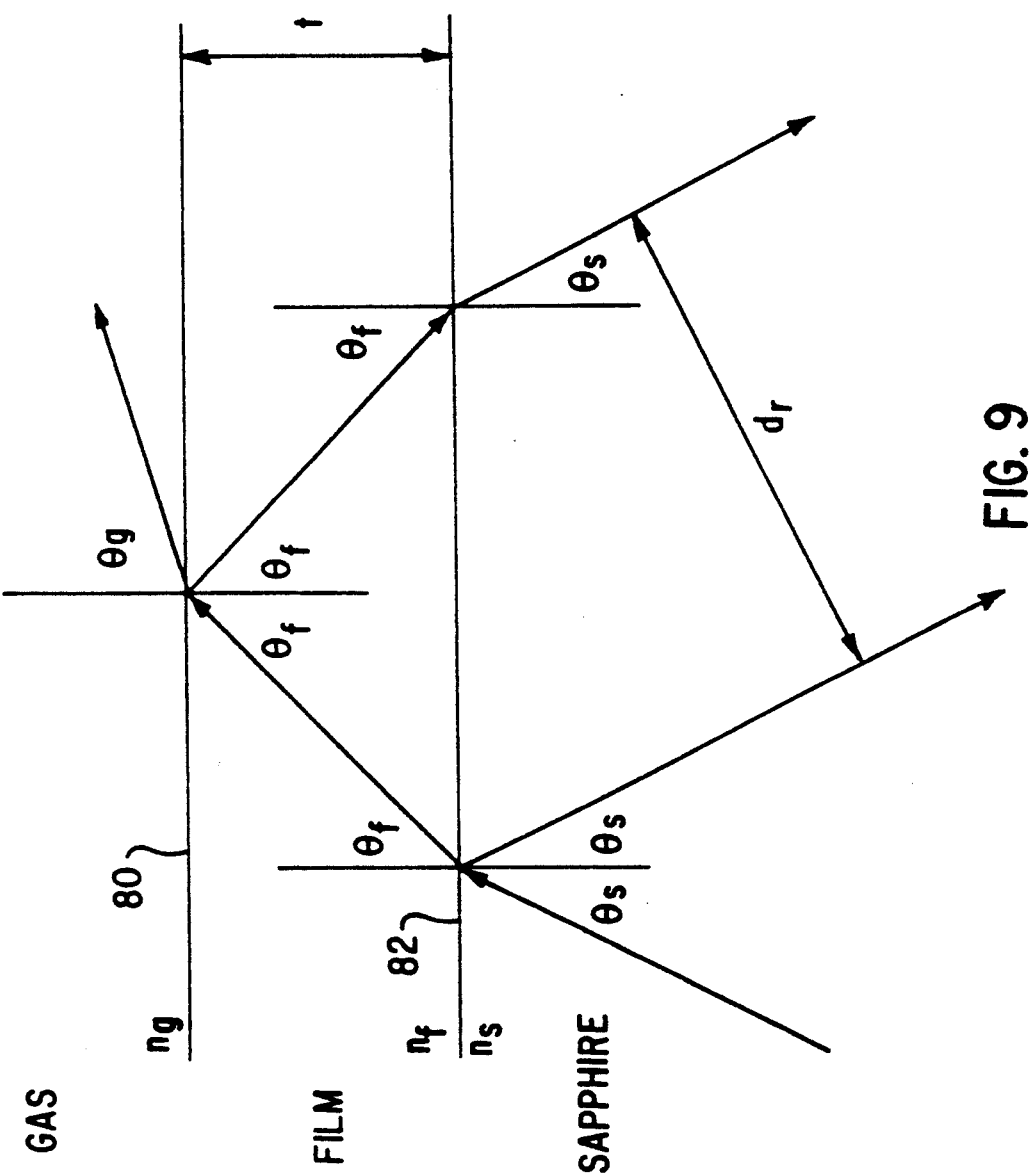
FIG. 9 illustrates the effect of a liquid film between the sapphire prism and the flow stream of FIG. 2.

FIG. 9 illustrates the effects of a liquid film between the sapphire prism and the gas phase of FIG. 3. Basically, a liquid film between the sapphire prism and the gas phase displaces light rays a distance $D_r$, yet has no effect on the results obtained by the technique of this invention, as described below.

An interface 80 between the gas phase of the flow stream and the liquid film is assumed to be parallel to an interface 82 between the film and the sapphire prism 34. For a given angle of incidence, Snell's law can be used to relate the indices of refraction and angular variables for these dielectrics:

$$n_s \sin(\theta_s) = n_f \sin(\theta_f) = n_g \sin(\theta_g)$$

where the subscript s refers to the sapphire prism, the subscript f refers to the film having a thickness t, the subscript g refers to the gas phase of the flow stream, $\theta_s$, $\theta_f$, and $\theta_g$ are angles shown in FIG. 9, and correspond to angles of incidence of light rays. This equation shows that the film has no effect on the Snell's law relating angles and indices of refraction for the prism and gas alone. Thus, the critical angle for the angle of incidence in the prism is still $\sin^{-1}(n_g/n_s)$. However, the critical reflection does not occur at the interface 82 between the prism and the film, but at the interface 80 between the film and the gas phase. Consequently, the critically reflected light ray is displaced in the prism compared to the case in which no film is present between the prism and the gas phase. The displacement $d_r$ of the light ray in the film is:

$$d_r = t \frac{n_s \sin 2\theta_s}{\sqrt{n_f^2 - n_s^2 \sin^2 \theta_s}}$$

Though the light ray has been displaced a distance $d_r$, the results obtained by the invention are not affected, because this displacement is very slight (film thickness which is generally less than one detector width) and because this invention is not concerned with which detectors are illuminated by a ray of light, but the gas step increase that occurs between illuminated detectors. In the case of no film, the invention determines the gas step height that occurs between the Brewster angle, and the critical angle of gas, regardless of which particular detectors sense these angles. In the case of a thick film between the gas phase and the prism, the light ray would be displaced a distance $d_r$ such that the Brewster angle and the critical angle would be sensed by different detectors than those indicated in FIG. 4. However, the same gas step height would occur, which would be processed according to the technique of FIG. 7 and would, therefore, indicate the same percent gas volume as in the case of no film. For example, in the case of a thin film between the gas phase and the prism, where $n_s$ is 1.75, $n_f$ is 1.4 and $\theta_s$ (the critical angle) is 34.9 degrees, $d_r$ is equal to 1.68t. The thickness t of such a film is less than 200μ and the distance $d_r$ in this example is less than 336μ. Thus, the invention successfully detects the percent gas volume of a high pressure gas in a flow stream despite the presence of a liquid film on the prism for cases in which the index of refraction of borehole high pressure gases is different than the index of refraction for borehole liquids.

The invention concerns an apparatus and method for analyzing the composition of a fluid comprised of one or more of water, oil, and gas. However, while particular arrangements with light sources and optical elements are shown, it is evident that other light sources, such as ultraviolet or visible light sources, as well as other elements for guiding the light to and from the sample, such as lenses, may be utilized. Likewise, other elements for measuring the intensity of the reflected light rays could be utilized. Other gas volume fractions can be chosen to define the gas volume categories. If only one detector element is used, then the angular range would essentially be centered at the gas critical angle and would not include the Brewster angle. No light would be obtained from the gas Brewster angle (which is near the liquid Brewster angle) so no information is gained by including the Brewster angle. For multichannel operation the Brewster angle is included (desirable, but not necessary) to produce contrast. Further, while the invention was described as having data processing means on the surface of the formation 14, it will be appreciated that such processing means could be at least partially located downhole. Therefore, it will be apparent to those skilled in the art that other changes and modifications may be made to the invention as described in the specification without departing from the spirit and scope of the invention as so claimed.

I claim:

1. A borehole apparatus for categorizing volumes of gas in a multiphase fluid obtained from a formation, the fluid comprising at least one of oil, water, and gas, the apparatus comprising:
    containing means for containing the fluid;
    source means for transmitting light toward the fluid in the containing means;
    optical means for transmitting light from the source means to the fluid and having an interface with the containing means, the interface comprising a means for reflecting light from the source means at an angle of incidence within a range that extends from less than a Brewster angle to more than a critical angle of gas;
    detector means for detecting light which is reflected from the interface;
    storing means for storing information related to a plurality of categories of determined gas volumes of formation fluids; and
    processing means for obtaining data concerning the angle of incidence of the reflected light from the detector means and the information from the storing means and for determining a category of gas volume of the multiphase fluid in the containing means according to the data related to the angle of incidence of the reflected light using the Brewster angle of gas and the critical angle of gas.

2. The apparatus of claim 1, wherein the processing means is also for deriving curvature information of the fluid for use in determining a category of gas volume of the fluid.

3. The apparatus of claim 2, wherein the processing means is also for determining baseline information of the fluid for use in determining a category of gas volume of the fluid.

4. The apparatus of claim 3, wherein the processing means is also for analyzing gas step height to determine that the fluid has a gas volume within one of medium gas and relatively high gas categories.

5. The apparatus of claim 4, wherein the processing means is also for analyzing the curvature information and the baseline information with the gas step height to determine that the fluid has a gas volume within one of relatively low gas and no gas categories.

6. The apparatus of claim 5, wherein the detector means comprises a plurality of detector elements, each arranged to detect light having a corresponding angle of incidence within a range that extends from less then the Brewster angle to more than the critical angle of gas.

7. The apparatus of claim 6, wherein the source means comprises an infrared emitting diode.

8. The apparatus of claim 7, wherein the optical means comprises a prism substantially transparent to the light, the prism forming the interface with the fluid in the containing means.

9. The apparatus of claim 8, comprising a p-polarizer between the infrared emitting diode and the prism.

10. The apparatus of claim 9, comprising a focusing means for focusing the light from the p-polarizer onto the interface.

* * * * *